United States Patent [19]

Abass et al.

[11] Patent Number: 5,482,122
[45] Date of Patent: Jan. 9, 1996

[54] ORIENTED-RADIAL-CORES RETRIEVAL FOR MEASUREMENTS OF DIRECTIONAL PROPERTIES

[75] Inventors: Hazim H. Abass; Matthew E. Blauch, both of Duncan, Okla.; James J. Venditto, Sugar Land, Tex.

[73] Assignee: Halliburton Company, Dallas, Tex.

[21] Appl. No.: 352,469

[22] Filed: Dec. 9, 1994

[51] Int. Cl.⁶ .................................................. E21B 49/02
[52] U.S. Cl. .......................... 175/50; 73/153; 166/250.01
[58] Field of Search ................................. 175/50, 58, 20; 166/250; 73/153; 324/376

[56] References Cited

U.S. PATENT DOCUMENTS

| | | | |
|---|---|---|---|
| 4,751,646 | 6/1988 | Alger | 324/376 X |
| 4,790,180 | 12/1988 | Sinnokrot | 73/153 |
| 5,105,894 | 4/1992 | Enderlin | 175/44 |
| 5,253,719 | 10/1993 | Blauch et al. | 175/50 |
| 5,272,916 | 12/1993 | Blauch et al. | 73/151 |
| 5,277,062 | 1/1994 | Blauch et al. | 73/153 |
| 5,318,123 | 6/1994 | Venditto et al. | 166/250 |

*Primary Examiner*—Hoang C. Dang
*Attorney, Agent, or Firm*—Arnold White & Durkee

[57] ABSTRACT

A method for the determination of anisotropic material properties in subterranean rock formations by means of radially oriented and generally equally angularly spaced sidewall cores obtained by use of a rotary sidewall coring tool. The measurement values obtained from testing of the sidewall cores are utilized to obtain an accurate prediction of the shape of the ellipse that describes the variation in the material property under consideration as a function of direction in the bedding plane of the subterranean rock formation.

9 Claims, 3 Drawing Sheets

ORIENTED-RADIAL-CORES RETRIEVAL FOR MEASUREMENTS OF DIRECTIONAL PROPERTIES

BACKGROUND OF THE INVENTION

The present invention relates generally to the use of coring systems utilized in the oil and gas industries for the determination of material properties in subterranean rock formations; and more particularly relates to the use of cases obtained from predetermined directions proximate a wellbore to determine non-isotropic formation properties.

Anisotropy in rock properties results from inherent characteristics such as crystal orientation, microcrack distribution, and other microgeometric properties. It is well established that rock properties show a significant optional variation within the bedding plane as well as in the vertical direction perpendicular to the bedding plane. The evaluation of anisotropic properties within a formation has been recognized as a valuable aid in designing fracturing programs. Such evaluation is disclosed in U.S. Pat. No. 5,272,916, issued Dec. 28, 1993 to Blauch et al., the specification of which is hereby incorporated herein by reference.

For many applications a transversely isotropic model has been applied which assumes that rock properties within the bedding plane are isotropic. This model is unrealistic for many materials, particularly in the case of fine grained formations such as shales in which microscopic anisotropy within the bedding plane can be quite significant.

Prior art solutions to the problem of the determination of material properties in the bedding planes of subterranean rock formations have included the use of sidewall coring tools to obtain a single sample for a given bedding plane. Examples of such prior art sidewall coring tools are known to those skilled-in-the-art. The use of an exemplary tool is described in U.S. Pat. Nos. 5,105,894, issued Apr. 21, 1992 to Enderlin, and 5,253,719, issued Oct. 19, 1993 to Blauch et al; both assigned to the assignee of the present invention. The disclosures of each of those patents is hereby incorporated herein by reference for all purposes. Such tools have typically been utilized, however, to obtain only a single core sample at a given depth in the formation. It is not apparent that any effort has previously been made to obtain multiple core samples of essentially the same depth but at known azimuthal orientations, or to further use such core sample data to determine non-isotropic formation properties. Thus, the prior art solutions have been confined to a directionally isotropic model of material properties in such bedding planes.

The prior art solutions to the problem of the determination of material properties in subterranean rock formations have not included the use of a plurality of laterally spaced, directionally oriented core samples to thereby provide an accurate prediction of the material properties in a bedding plane as a function of the directional orientation parallel to the bedding plane.

The present invention overcomes the problem of the determination of material properties in subterranean rock formations by permitting the determination of anisotropic material properties in bedding planes of such subterranean rock formations by use of a sidewall coring tool to obtain radially oriented, and preferably generally equally angularly spaced core samples to thereby provide an accurate prediction of the material properties as a function of directional orientation within a bedding plane.

SUMMARY OF THE INVENTION

The present invention finds utility in oil and gas exploration where it is necessary to determine properties in subterranean rock formations such as, for example, the reservoir permeability within a given generally horizontal plane, thereby enabling the efficient extraction of oil and gas reserves. Also, the mechanical and physical properties such as Young's modulus, Poisson's ratio and permeability within the bedding plane play an important role in wellbore instability problems and well productivity.

The present invention utilizes a method for determining the material properties of subterranean rock formations whereby a rotary sidewall coring tool is utilized to obtain radially oriented and equally angularly spaced core samples from the sidewall of an open wellbore. An orienting assembly is utilized to orient the coring tool in each of a plurality of azimuthal directions to facilitate the obtaining the cores at the desired angular spacing. The subsequent testing of the core samples then provides measurements of material properties at equally spaced radial directions within the bedding plane, thereby providing a means of accurately predicting the variation of material properties as a function of direction within the bedding plane from which the samples were taken.

DETAILED DESCRIPTION OF THE INVENTION

A method is described which is particularly useful for the determination of material properties directionally within the horizontal plane of subterranean rock formations such as, for example, the permeability in an oil or gas field. The present invention enables the determination of anisotropic material properties of such subterranean rock formations, and the tensor(s) for the properties within the formation, thereby enabling the efficient extraction of oil and gas reserves. As will be apparent from the following detailed description, the inventive concepts disclosed herein are applicable to numerous other applications where it is desired to determine the variation in material properties generally within a plane of a subterranean formation. In the description, like elements in the various FIGURES will be designated by the same numerical designations.

A presently preferred embodiment of the invented apparatus is used advantageously in an open wellbore for the determination of material properties in subterranean formations such as, for example, the permeability of such formations to the flow of oil and/or gas.

Figure 1:
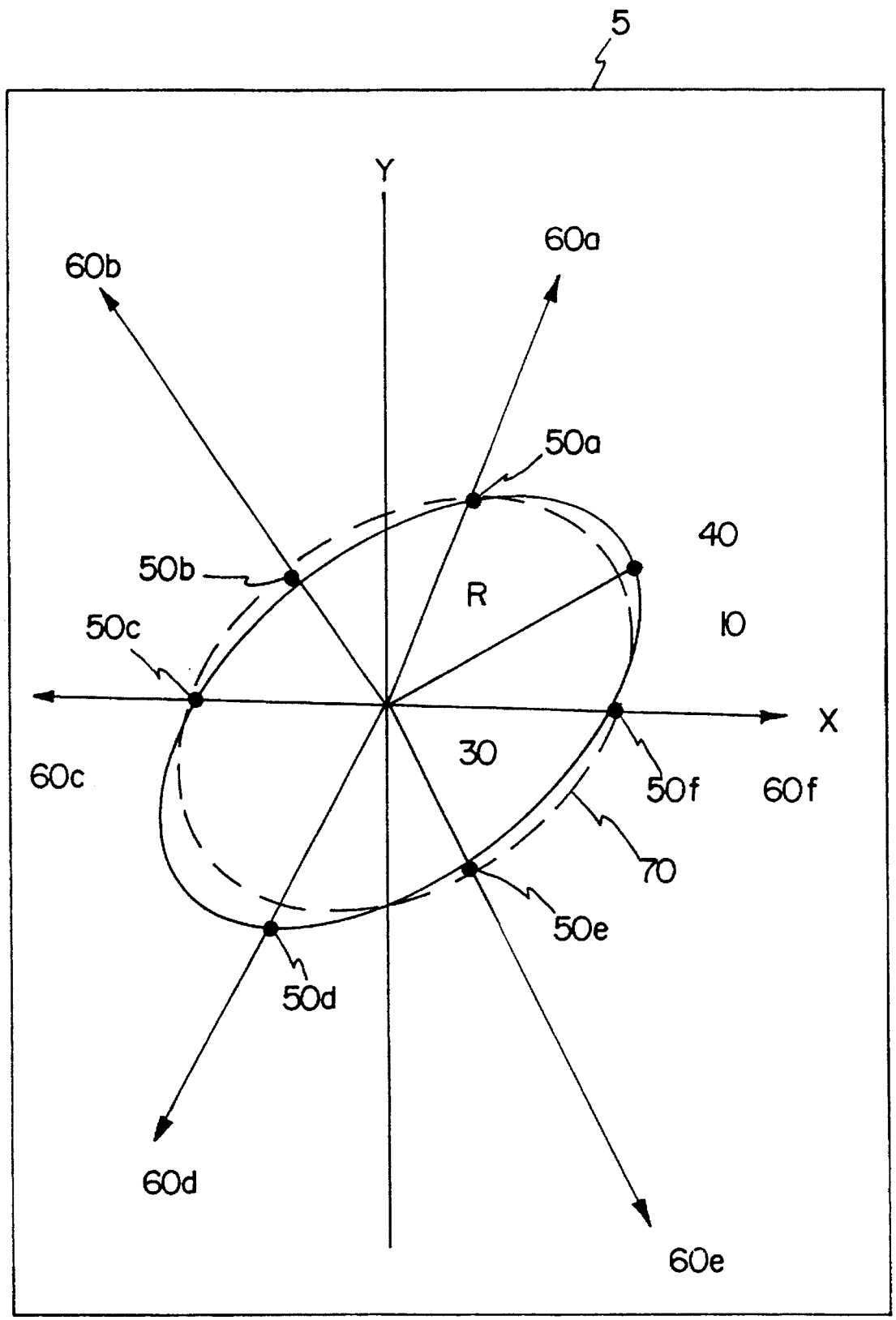
FIG. 1 is a graphical illustration of the anisotropic nature of material properties in subterranean rock formations within a bedding plane.

The presently preferred embodiment of the subject invention is now described with reference to FIG. 1. In subterranean rock formations material properties are typically directionally anisotropic in the bedding or horizontal plane circumferentially around the borehole 5. Examples of such properties include permeability, acoustic velocity, Young's modulus, Poisson's ratio, shear modulus, compressive strength, and tensile strength. Such variations in an individual material property can be represented by an ellipse 10 wherein the radial distance R from the center point 30 to a given point 40 on the ellipse 10 represents the magnitude of the material property in the direction represented by θ in the bedding plane 5. As already discussed, for a given formation, there will be any number of material properties that will be anisotropic in nature. Thus for any given subterranean formation, the set of material properties under consideration will constitute a tensor (a generalized vector whose component values are function of a direction in space).

A prediction 70 (illustrated by a dashed line) of the actual shape of the ellipse 10 for a given material property is obtained by means of measurements 50a–50f of the material property taken at equally spaced angular directions 60a–60f in the bedding plane 5. Such a prediction 70 of the actual shape of the ellipse 10 is finally obtained by fitting a curve through the resulting measurements 50a–50f using conventional curve fitting computations. As more measurements are utilized the resulting prediction 70 of the actual shape of the ellipse 10 will become more accurate.

The measurement values are obtained by using conventional testing methods, according to ASTM standards, upon core samples. By way of example, permeability of the core sample formation may be determined by testing the core sample in accordance with an API recommended test procedure (RP-40). Similarly by way of example, Young's modulus may be determined by standard D3148 in accordance with ASTM. The individual core samples themselves are obtained by means of a rotary sidewall coring tool (RSCT) having the capability for precise orientation of the coring tool. Such a RSCT is disclosed in U.S. Pat. No. 5,105,894 the disclosure of which is hereby incorporated herein by reference. The rotary sidewall coring tool may be oriented in each desired direction through use of a rotating and orienting assembly as is disclosed in U.S. Pat. No. 5,318,123, issued Jun. 7, 1994 to Venditto et al. The disclosure of U.S. Pat. No. 5,318,123 is hereby incorporated by reference for all purposes. Briefly, this rotating and orienting assembly includes an orienting assembly sufficient to determine an azimuth relative to magnetic north, and a motorized rotating assembly to selectively rotate the coring tool to a desired orientation relative thereto.

Figure 2:
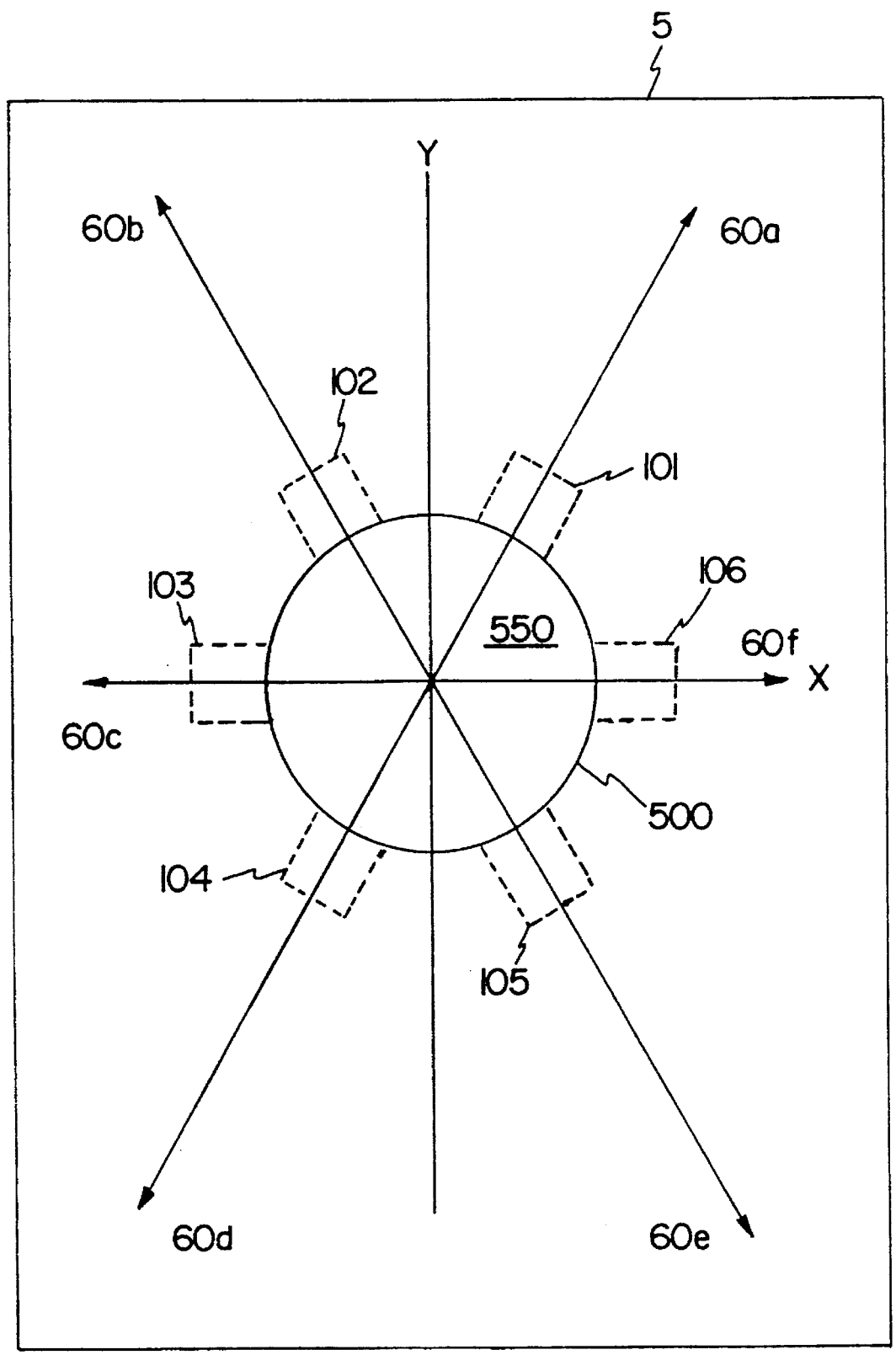
FIG. 2 is a schematic diagram illustrating the use of six equally spaced and radially oriented sidewall cores for the determination of anisotropic material properties in subterranean rock formations.

With reference to FIG. 2, the use of sidewall core samples to provide the prediction 70 of the shape of the ellipse 10 is now described. In FIG. 2 is shown the location of six core samples 101–106, taken from the sidewall 500 of an open well bore hole 550, and equally spaced in the bedding plane 5 at 60 degree intervals and oriented in directions 60a–60f. It has been found that six measurement values is the minimum number required in order to provide a reasonably accurate prediction 70 of the shape of the ellipse 10. Numerical techniques based on functional approximation can be applied to determine the best fitting ellipse for the measured data. Tensorial properties can be described by an ellipse which can be defined for a porous medium, if directional cores are retrieved.

Figure 3:
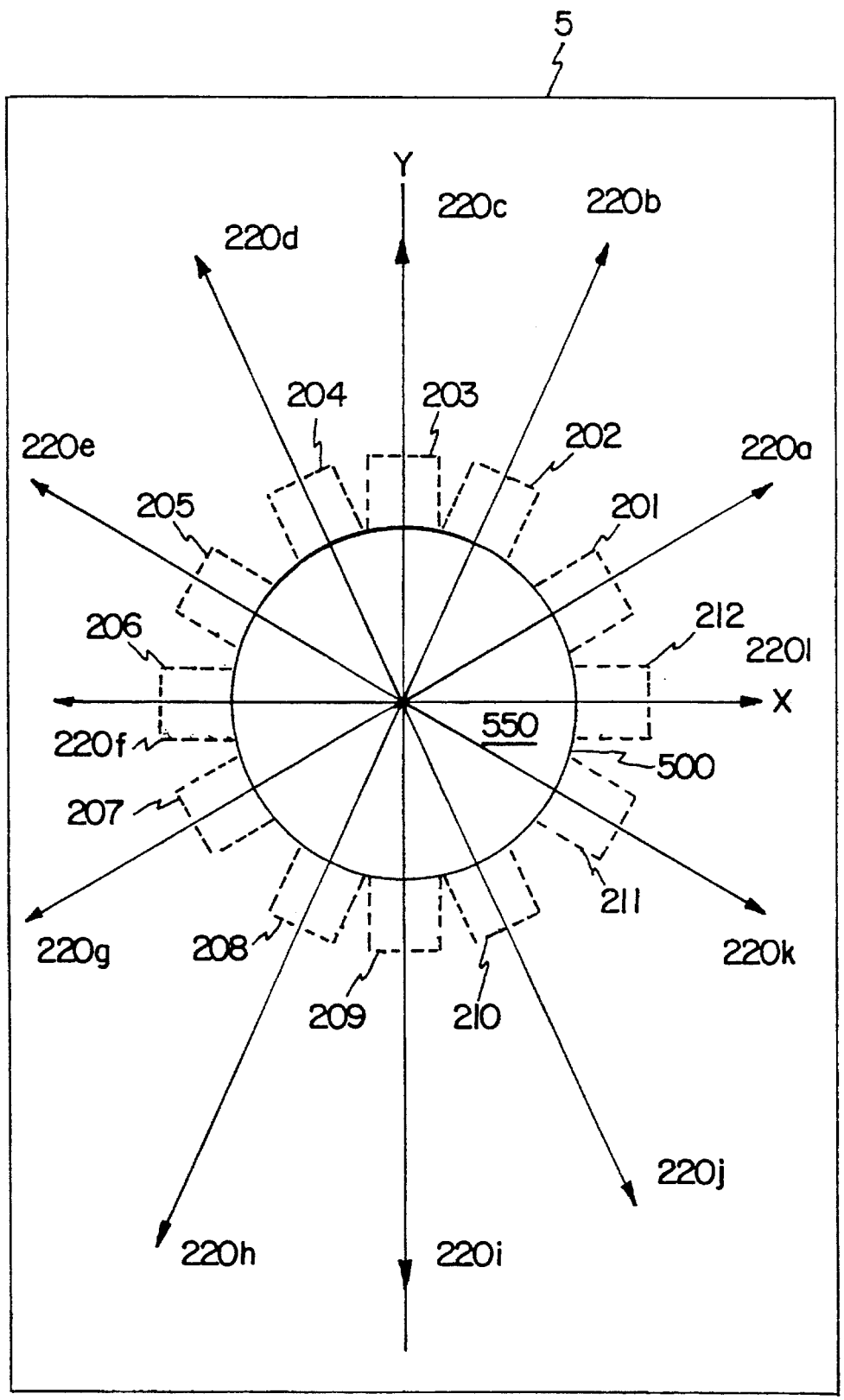
FIG. 3 is a schematic diagram illustrating the use of twelve equally spaced and radially oriented sidewall cores for the determination of anisotropic material properties in subterranean rock formations.

With reference to FIG. 3, the optimum use of sidewall core samples to provide the prediction 70 of the shape of the ellipse 10 for a given material property is now described. In FIG. 3 is shown the location of twelve core samples 201–212, taken from the sidewall 500 of an open well bore hole 550, and equally spaced in the bedding plane 5 at 30 degree intervals and oriented in directions 220a–220l. It has been found that the use of twelve measurement values provides an extremely accurate prediction of the shape of the ellipse 10 using conventional curve fitting computations, and represents the optimum trade-off between the time and expense of obtaining the core samples vs. the value of the information extracted.

A method of determining material properties has been described for use in oil and gas exploration for the determination of material properties of subterranean rock formations such as, for example, the permeability to oil and gas flow within such formations. A preferred implementation of the method employs the use of a RSCT to obtain radially oriented and equally angularly spaced core samples to thereby permit the accurate prediction of material properties as a function of direction within the bedding plane from which the samples are obtained.

The present invention will thus provide an accurate prediction of anisotropic material properties in bedding planes of subterranean rock formations thereby greatly enhancing the design of drilling programs for oil and gas exploration.

While the invention has been particularly shown and described with reference to preferred embodiments for use in oil and gas exploration, it should be understood that persons skilled in the art may make various changes in form and detail of the present invention without departing from the spirit and scope of the invention; and further, that the principles disclosed are susceptible of other applications which will be apparent to those skilled in the art. This invention, therefore, is not intended to be limited to the particular embodiments herein disclosed.

What is claimed is:

1. A method for the determination of anisotropic material properties within a generally horizontal plane of a subterranean rock formation, comprising the steps of:

extracting a plurality of radially oriented core samples from the sidewall of an open well borehole within a given horizontal plane;

testing said core samples to determine a measurement of at least one material property of each core sample;

estimating the anisotropic distribution of said material property within said horizontal plane in response to said determined measurements of said material property.

2. The method of claim 1, wherein said step of estimating the anisotropic distribution of said material property comprises the steps of:

graphically depicting said estimated material properties; and predicting the shape of an ellipse on said graphic depiction for said anisotropic distribution of said material property within said horizontal plane.

3. The method of claim 1, wherein the plurality of radially oriented core samples from the sidewall of the open well borehole are generally equally angularly spaced.

4. The method of claim 3, wherein the spacing of the radially oriented core samples is generally within the range of 30 to 60 degrees.

5. The method of claim 1, wherein the material properties are selected from the group consisting of permeability, Young's modulus, Poisson's ratio, shear modulus, compression strength, and tensile strength.

6. The method of claim 1, wherein the number of measurement locations is in the range of from 6 to 12.

7. The method of claim 2, wherein the step of predicting the shape of said ellipse for said material property comprises the steps of:

creating data points for each measurement consisting of the measured property values and the angular location of the corresponding core sample; and deriving curves passing through each of said data points that represent predictions of the actual shape of the ellipse for said material property.

8. A method for the determination of anisotropic material properties within a generally planar region of a subterranean rock formation, comprising the steps of:

extracting 6 to 12 radially oriented and generally equally angularly spaced core samples from the sidewall of a borehole penetrating said formation; and obtaining a measurement of at least one material property for each core sample;

predicting the shape of the ellipse for the anisotropic distribution of said material property within said generally planar region.

9. The method of claim 8, wherein said material property is selected from the group consisting of permeability, Young's modulus, Poisson's ratio, shear modulus, compressive strength and tensile strength.

* * * * *